US011880104B2

(12) United States Patent
Stover et al.

(10) Patent No.: US 11,880,104 B2
(45) Date of Patent: Jan. 23, 2024

(54) REFLECTIVE POLARIZER AND DISPLAY SYSTEM INCLUDING SAME

(71) Applicant: 3M INNOVATIVE PROPERTIES COMPANY, St. Paul, MN (US)

(72) Inventors: Carl A Stover, St. Paul, MN (US); Robert D. Taylor, Stacy, MN (US); Bharat R. Acharya, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 18/247,209

(22) PCT Filed: Sep. 10, 2021

(86) PCT No.: PCT/IB2021/058253
§ 371 (c)(1),
(2) Date: Mar. 29, 2023

(87) PCT Pub. No.: WO2022/079507
PCT Pub. Date: Apr. 21, 2022

(65) Prior Publication Data
US 2023/0350244 A1    Nov. 2, 2023

Related U.S. Application Data

(60) Provisional application No. 63/092,032, filed on Oct. 15, 2020.

(51) Int. Cl.
*G02F 1/1335*    (2006.01)
*G06V 10/143*    (2022.01)
*G02F 1/1333*    (2006.01)

(52) U.S. Cl.
CPC .... *G02F 1/133536* (2013.01); *G02F 1/13338* (2013.01); *G06V 10/143* (2022.01)

(58) Field of Classification Search
CPC .......... G02F 1/133536; G02F 1/13338; G06V 10/143
(Continued)

(56) References Cited

U.S. PATENT DOCUMENTS 5,831,375 A    11/1998  Benson, Jr.
5,882,774 A     3/1999  Jonza et al.
(Continued)

FOREIGN PATENT DOCUMENTS

WO    2020035768 A1    2/2020
WO    2020067243 A1    4/2020
WO    2022016445 A1    1/2022

OTHER PUBLICATIONS

International Search Report for PCT International Application No. PCT/IB2021/058253, dated Nov. 16, 2021, 3 pages.

*Primary Examiner* — Charles S Chang
(74) *Attorney, Agent, or Firm* — Clifton F. Richardson

(57) ABSTRACT

A reflective polarizer has a transmittance for a first polarization state having a band edge separating a first wavelength range extending at least from about 450 nm to about 900 nm and a second wavelength range extending at least from about 1100 nm to about 1300 nm. For the first polarization state, the reflective polarizer has an average transmittance in the first wavelength range less than about 10% and an average transmittance in the second wavelength range greater than about 80%; and for a second polarization state, the reflective polarizer has an average transmittance in the first wavelength range greater than about 40% and an average transmittance in the second wavelength range greater than about 80%. A display system includes the reflective polarizer and an infrared light source configured to emit an infrared light having a wavelength W1. The band edge has a band edge wavelength W2>W1.

15 Claims, 17 Drawing Sheets

(58) Field of Classification Search
USPC .............................................. 349/12, 96–98
See application file for complete search history.

(56) References Cited

U.S. PATENT DOCUMENTS

| | | |
|---|---|---|
| 6,179,948 B1 | 1/2001 | Merrill et al. |
| 6,783,349 B2 | 8/2004 | Neavin et al. |
| 6,967,778 B1 | 11/2005 | Wheatley et al. |
| 9,162,406 B2 | 10/2015 | Neavin et al. |
| 9,441,809 B2 | 9/2016 | Nevitt et al. |
| 9,551,818 B2 | 1/2017 | Weber et al. |
| 2005/0122308 A1 | 6/2005 | Bell et al. |
| 2011/0090177 A1 | 4/2011 | Chuang et al. |
| 2019/0391307 A1 | 12/2019 | Wheatley et al. |
| 2022/0091316 A1* | 3/2022 | Long .................... G02B 5/0294 |

* cited by examiner

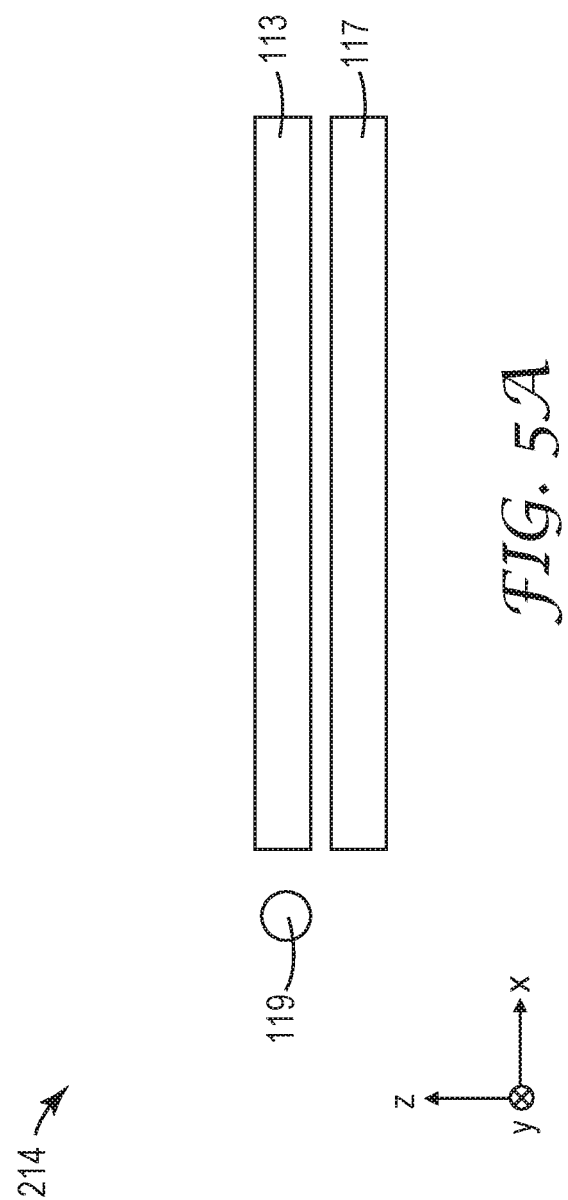

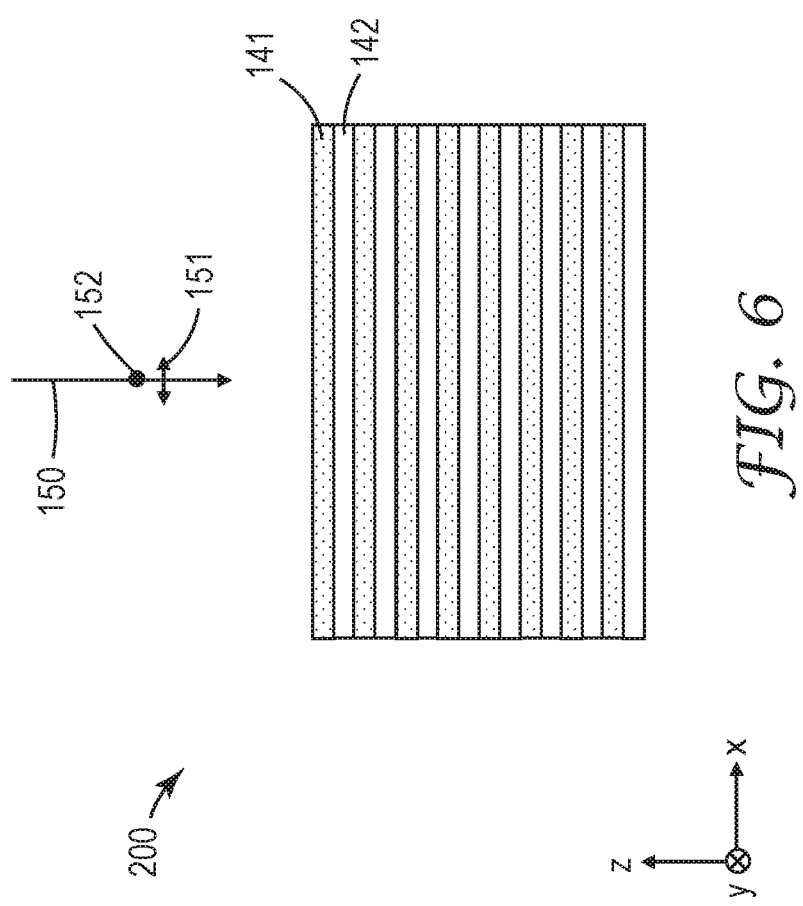

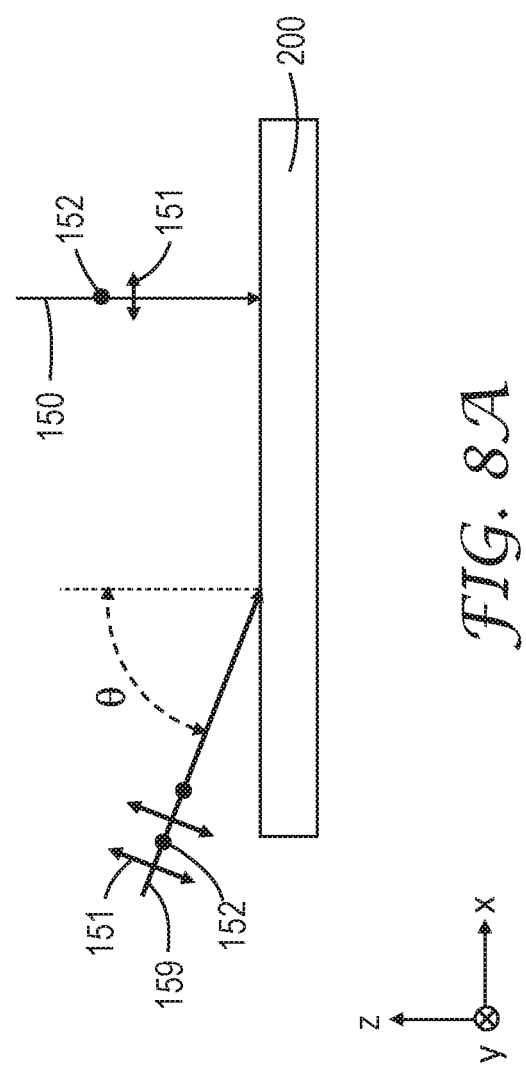

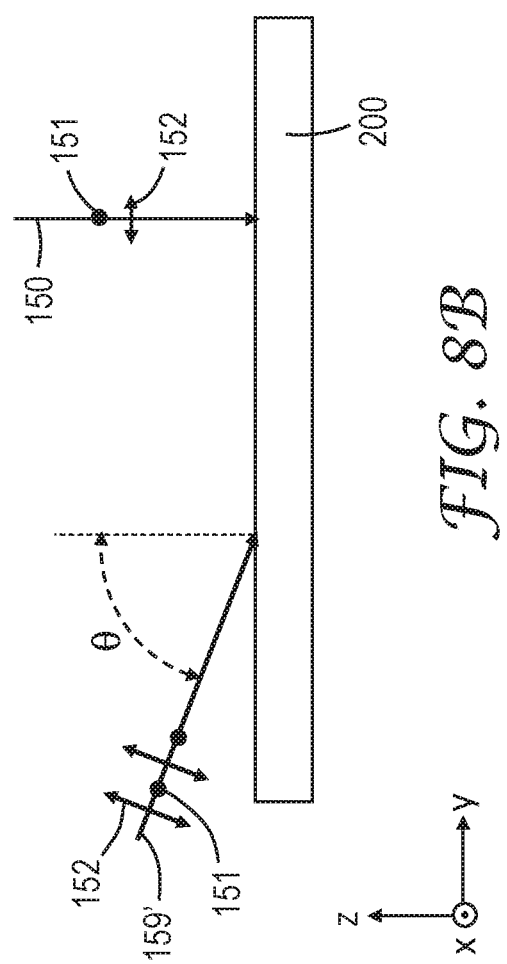

REFLECTIVE POLARIZER AND DISPLAY SYSTEM INCLUDING SAME

CROSS REFERENCE TO RELATED APPLICATIONS

This application is a national stage filing under 35 U.S.C. 371 of PCT/IB2021/058253, filed Sep. 10, 2021, which claims the benefit of U.S. Application No. 63/092,032, filed Oct. 15, 2020, the disclosures of which are incorporated by reference in their entirety herein.

BACKGROUND

A display system, such as a liquid crystal display system, can include a reflective polarizer. The reflective polarizer can be a collimating reflective polarizer.

A display system can include an infrared light source and sensor for fingerprint detection.

SUMMARY

The present description generally relates to reflective polarizers and display systems. The reflective polarizer may be a collimating reflective polarizer having a higher transmission for normally incident light than for obliquely incident light. The display system can include the reflective polarizer, a display panel, and an infrared light source. The reflective polarizer may be configured to provide a low color shift with viewing angle that is robust against manufacturing variations while allowing a high transmittance of infrared light from the infrared light source.

According to some aspects of the present description, a display system for sensing a finger of a user applied to the display system is provided. The display system includes a display panel configured to generate an image for viewing by the user; a sensor for sensing the finger of the user disposed proximate the display panel; an infrared light source configured to emit an infrared light having a wavelength W1 toward the finger of the user; and a reflective polarizer disposed between the display panel and the sensor. The sensor is configured to receive and detect at least a portion of the infrared light reflected by the finger. For substantially normally incident light and for a first polarization state, an optical transmittance of the reflective polarizer has a first band edge separating first and second wavelength ranges, where the first wavelength range extends at least from about 450 nm to about 900 nm and the second wavelength range extends at least from about 1100 nm to about 1300 nm. For substantially normally incident light and for a first polarization state, the reflective polarizer has an average optical transmittance in the first wavelength range of less than about 10% and an average optical transmittance in the second wavelength range of greater than about 80%. For substantially normally incident light and for a second polarization state orthogonal to the first polarization state, the reflective polarizer has an average optical transmittance in the first wavelength range of greater than about 40% and an average optical transmittance in the second wavelength range of greater than about 80%. In some embodiments, the first band edge has a band edge wavelength W2 corresponding to an optical transmittance of about 50% along the first band edge, where W2>W1. In some such embodiments, or in other embodiments, W1<975 nm and the reflective polarizer is configured such that for substantially white incident light and for the second polarization state, a maximum difference in color between light transmitted through the reflective polarizer and the incident light as an angle of incidence of the incident light varies from zero to about 60 degrees in each of a plane of incidence parallel to the second polarization state and a plane of incidence orthogonal to the second polarization state is no more than about 0.07 on a CIE 1931 xy color space.

According to some aspects of the present description, a reflective polarizer including a plurality of alternating polymeric layers numbering at least 10 in total where each polymeric layer has an average thickness less than about 500 nm is provided. For substantially normally incident light and for a first polarization state, the reflective polarizer has an average optical transmittance in a first wavelength range extending from about 425 nm to about 650 nm of less than about 5%. For substantially normally incident light and for a second polarization state orthogonal to the first polarization state, the reflective polarizer has an average optical transmittance T1 in the first wavelength range of greater than about 40%. For light incident on the reflective polarizer at an angle of incidence of about 60 degrees and for the first polarization state and a plane of incidence parallel to the first polarization state, the reflective polarizer has an average optical transmittance in the first wavelength range of less than about 5%. For light incident on the reflective polarizer at an angle of incidence of about 60 degrees and for the second polarization state and a plane of incidence parallel to the second polarization state, an optical transmittance of the reflective polarizer has a first band edge separating the first wavelength range and a second wavelength range extending at least from about 850 nm to about 1100 nm, where a best linear fit to the first band edge correlating the optical transmittance to wavelength at least across a wavelength range where the optical transmittance increases from about 20% to about 80% has a slope of greater than about 3%/nm and an r-squared value of greater than about 0.9, and a best second order polynomial fit to the optical transmittance in the first wavelength range has a negative second order coefficient and an r-squared value of greater than about 0.9. For light incident on the reflective polarizer at an angle of incidence of about 60 degrees and for the second polarization state and a plane of incidence parallel to the second polarization state, the reflective polarizer having an average optical transmittance T2 in the first wavelength range from about 15% to about 35% and an average optical transmittance in the second wavelength range greater than about 80%. T1−T2≥10%.

These and other aspects will be apparent from the following detailed description. In no event, however, should this brief summary be construed to limit the claimable subject matter.

BRIEF DESCRIPTION OF THE DRAWINGS

FIGS. 5A-5B are schematic cross-sectional views of illustrative extended illumination sources.

FIG. 6 is a schematic cross-sectional view of an illustrative reflective polarizer.

FIGS. 8A-8B are schematic illustrations of planes of incidence.

DETAILED DESCRIPTION

In the following description, reference is made to the accompanying drawings that form a part hereof and in which various embodiments are shown by way of illustration. The drawings are not necessarily to scale. It is to be understood that other embodiments are contemplated and may be made without departing from the scope or spirit of the present description. The following detailed description, therefore, is not to be taken in a limiting sense.

According to some embodiments of the present description, a display system includes a reflective polarizer having a band edge wavelength greater than the wavelength of an infrared light used in the display system for sensing a finger (e.g., for detecting a fingerprint) of a user applied to the display system. The reflective polarizer used in display systems with finger sensors has conventionally been selected to have a band edge below the wavelength of the infrared light used for finger sensing. However, this can cause an undesired color shift at high viewing angles (e.g., greater than about 60 degrees) due to manufacturing variations which cause the band edge to shift to sufficiently low wavelengths for some regions of the film to significantly affect the color shift. Furthermore, having the band edge below the wavelength of the infrared light can result in undesired color shift at very high viewing angles (e.g., about 75 degrees or higher) even if there were no manufacturing variations. Moving the band edge to higher wavelengths can reduce or eliminate regions of the film resulting in undesired color shift but results in reduced transmission of infrared light in conventional display systems. According to some embodiments of the present description, the display system can be configured such that the infrared light is incident on the reflective polarizer at an oblique angle of incidence so that the band edge of the reflective polarizer shifts to less than the infrared wavelength at the oblique angle of incidence. This allows for low color shift with viewing angle even when manufacturing variations occur and/or even for very high viewing angles without substantially reducing transmission of the infrared light through the reflective polarizer. Moreover, according to some embodiments, the reflective polarizer has a transmission spectrum for obliquely incident light having a shape that results in further reduced color shift with viewing angle.

Figure 1A:
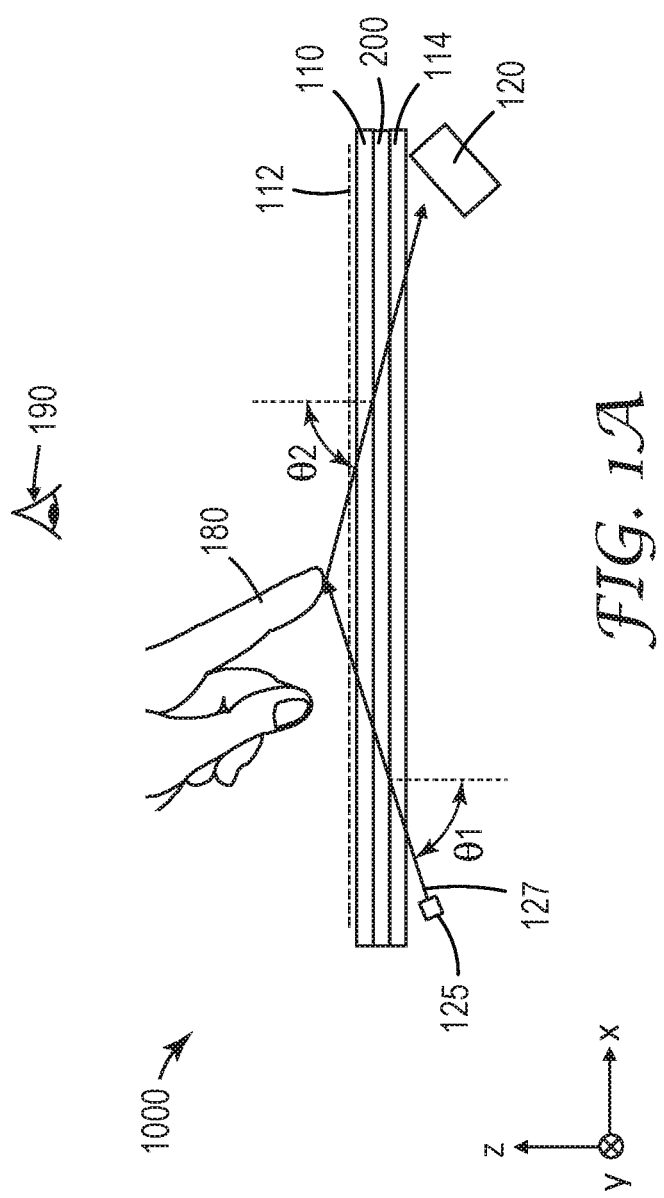
FIGS. 1A-1B are schematic cross-sectional views of illustrative displays systems.
Figure 1B:
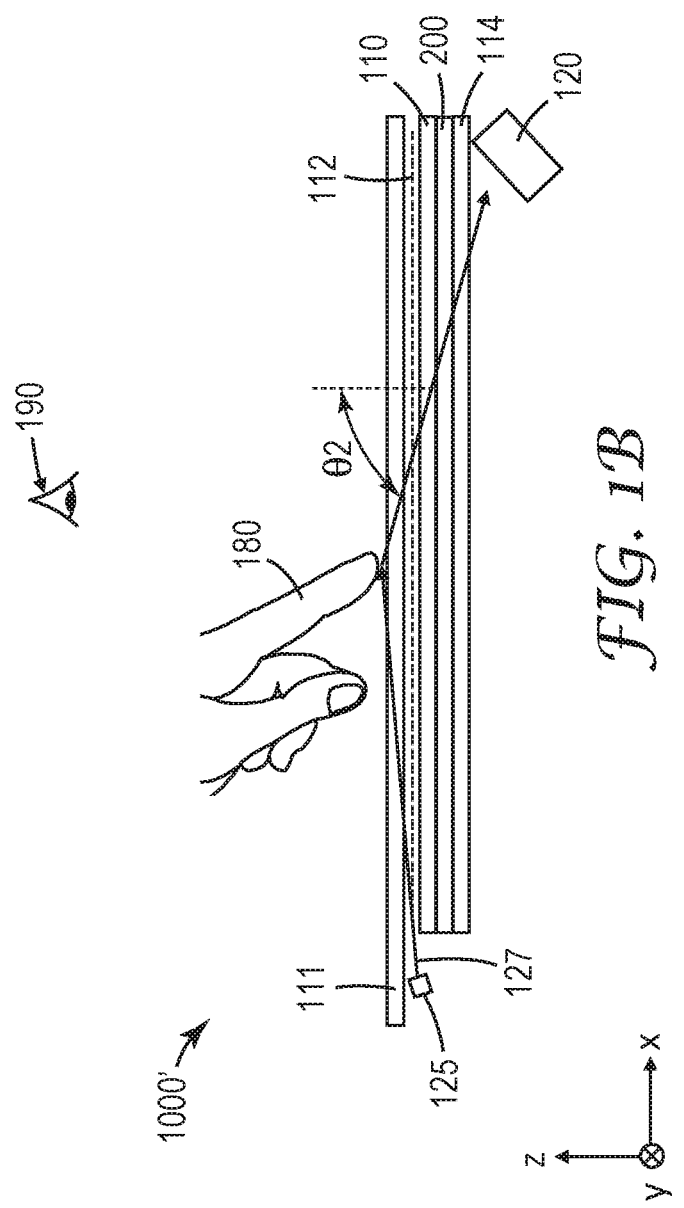

FIGS. 1A-1B are schematic cross-sectional views of displays systems 1000, 1000' for sensing a finger 180 of a user 190 applied to the display system 1000, 1000' according to some embodiments. The display system 1000, 1000' includes a display panel 110 configured to generate an image 112 for viewing by the user 190; a sensor 120 for sensing the finger 180 of the user 190 disposed proximate the display panel 110; an infrared light source 125 configured to emit an infrared light 127 having a wavelength W1 (see, e.g., FIGS. 3 and 9) toward the finger 180 of the user 190, where the sensor 120 is configured to receive and detect at least a portion of the infrared light 127 reflected by the finger 180; and a reflective polarizer 200 disposed between the display panel 110 and the sensor 120 such that the reflective polarizer 200 has any of the transmittance properties described elsewhere herein. For example, in some embodiments, for substantially normally incident light: for a first polarization state, an optical transmittance of the reflective polarizer has a first band edge separating first and second wavelength ranges, where the first wavelength range extends at least from about 450 nm to about 900 nm and the second wavelength range extends at least from about 1100 nm to about 1300 nm, and where the reflective polarizer has an average optical transmittance in the first wavelength range of less than about 10% and an average optical transmittance in the second wavelength range of greater than about 80%; and for a second polarization state orthogonal to the first polarization state, the reflective polarizer has an average optical transmittance in the first wavelength range of greater than about 40% and an average optical transmittance in the second wavelength range of greater than about 80%. In some embodiments, for substantially normally incident light and for a first polarization state, the reflective polarizer 200 has a first band edge separating first and second wavelength ranges and having a band edge wavelength W2 corresponding to an optical transmittance of about 50% along the first band edge. In some embodiments, the reflective polarizer 200 is configured such that for substantially white incident light and for the second polarization state, a maximum difference in color between light transmitted through the reflective polarizer and the incident light as an angle of incidence (angle relative to surface normal) of the incident light varies from zero to about 60 degrees in each of a plane of incidence (plane defined by the light propagation direction and the surface normal) parallel to the second polarization state and a plane of incidence orthogonal to the second polarization state is no more than about 0.07 on a CIE 1931 xy color space. In some embodiments, W2>W1.

In some embodiments, the infrared light 127 is first incident on the reflective polarizer at an angle of incidence θ1 greater than about 40 degrees (e.g., in a range of about 40 degrees to about 80 degrees or about 45 degrees to about 70 degrees). In some embodiments, the sensor 120 is disposed to receive light reflected from the finger and then incident on the reflective polarizer at an angle of incidence θ2 greater than about 40 degrees (e.g., in a range of about 40 degrees to about 80 degrees or about 45 degrees to about 70 degrees). For the display system 1000, the infrared light 127 is transmitted through the reflective polarizer 200, reflected from the finger 180, transmitted back through the reflective polarizer 200, and then received by the sensor 120. For the display system 1000', the infrared light 127 is transmitted to the finger 180 without being first transmitted through the reflective polarizer 200 and is then reflected from the finger 180, transmitted through the reflective polarizer 200, and then received by the sensor 120. In this case, the infrared light 127 is first incident on the reflective polarizer at an angle of incidence θ2. In some embodiments, the display system includes a cover glass 111, where the display panel 110 is disposed between the cover glass 111 and the reflective polarizer 200.

Figure 2:
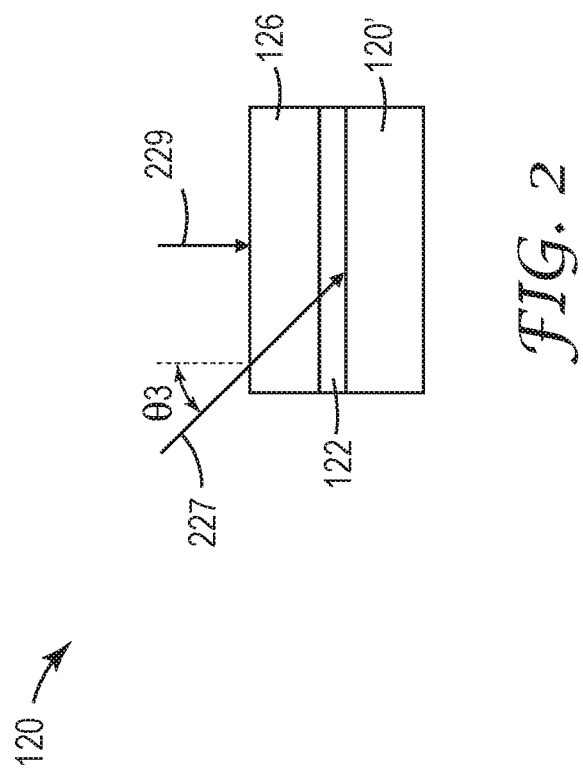
FIG. 2 is a schematic cross-sectional view of an illustrative sensor.

FIG. 2 is a schematic cross-sectional view of a sensor 120 according to some embodiments. The sensor 120 may be an infrared sensor sensitive to the wavelength W1. The sensor 120 includes a sensor 120' and may further include a wavelength selective optical filter 122 and/or an angularly selective optical filter 126. Alternatively, the optical filter 122 and/or 126 may be considered to be separate elements disposed on or proximate to the sensor. The optical filter 122 may be disposed between the optical filter 126 and the sensor 120', or the optical filter 126 may be disposed between the optical filter 122 and the sensor 120'. One or both of the optical filters 126 and 122 may optionally be omitted. The sensor 120' may be or include a photodiode, for example. In some embodiments, the sensor 120 includes an angularly selective optical filter 126 adapted to substantially transmit light 227 incident on the sensor at an oblique angle of incidence and substantially block light 229 normally incident on the sensor. In some such embodiments, or in other embodiments, the sensor 120 includes a wavelength selective optical filter 122 that substantially transmits the wavelength W1 and substantially blocks visible wavelengths and/or near infrared wavelengths more than 100 nm greater than W1. The angularly selective optical filter 126 may include an array of microlenses and an optically opaque mask layer with through holes (e.g., pinholes) therein where the through holes are in one-to-one correspondence with the microlenses and are offset (along the mask layer) relative to the microlenses such that the optical filter 126 primarily transmits obliquely incident light. Such optical filters are known in the art and are described in International Appl. Pub. No. WO 2020/035768 (Yang et al.), for example. The wavelength selective optical filter 122 may include a layer with dyes and/or pigments and/or may include an interference filter.

Figure 3:
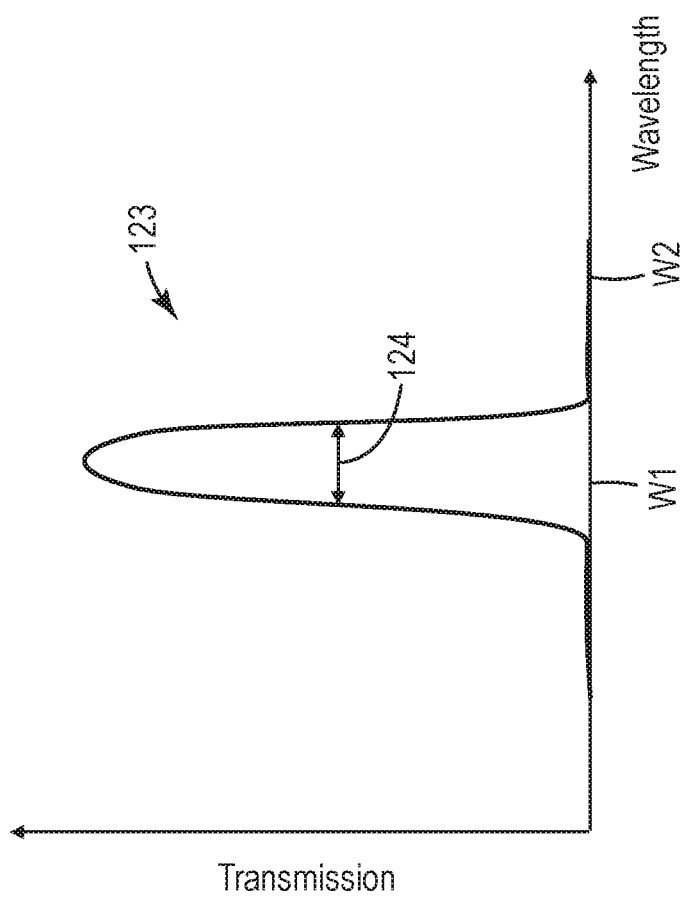
FIG. 3 is a schematic plot of transmission through an illustrative optical filter versus wavelength.

FIG. 3 is a schematic plot of transmission through the optical filter 122 according to some embodiments. In some embodiments, the optical filter 122 includes a passband 123 having a full-width at half-maximum 124 of less than about 100 nm, or less than about 80 nm. In some embodiments, the optical filter 122 substantially transmits the wavelength W1 and substantially blocks the wavelength W2.

Figure 4:
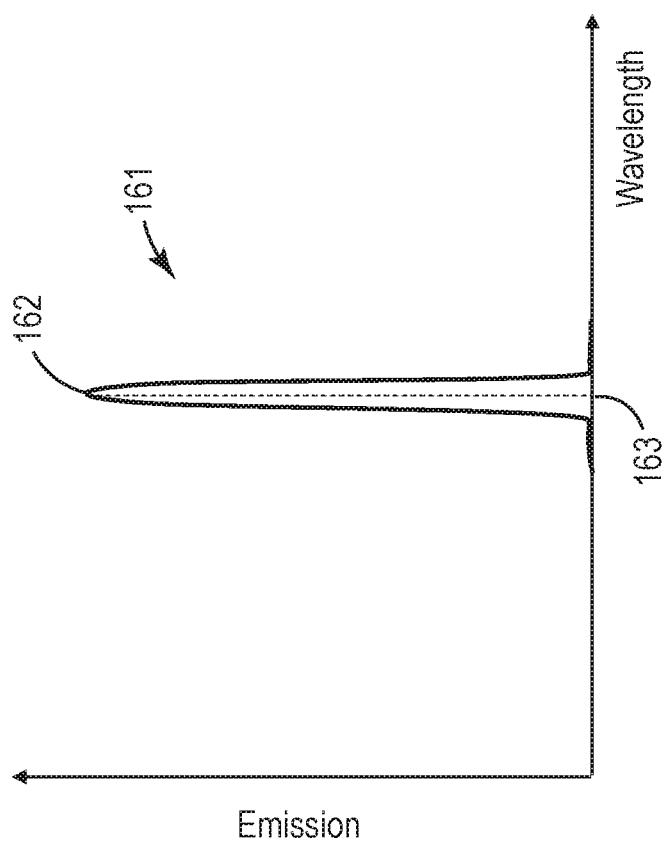
FIG. 4 is a schematic plot of emission from an infrared light source versus wavelength.

FIG. 4 is a schematic plot an emission 161 from an infrared light source 125 versus wavelength. The emission 161 has a peak 162 at a peak emission wavelength 163. The wavelength W1 of the light emitted by the infrared light source can be the peak emission wavelength 163. In some embodiments, the emission 161 has a full width at half maximum of less than about 20 nm, or less than about 10 nm, or less than about 7 nm. In some embodiments, the infrared light source 125 is a laser diode, for example. In some embodiments, the infrared light source 125 is a near-infrared light emitting diode.

In some embodiments, the display panel 110 is a liquid crystal display panel. Such display panels typically utilize an extended illumination source (e.g., a backlight) to provide light to the display panel. In some embodiments, the display system 1000, 1000' includes an extended illumination source 114, where the reflective polarizer 200 is disposed between the extended illumination source 114 and the display panel 110. In some embodiments, the reflective polarizer 200 is a collimating reflective polarizer. Such polarizers can provide a collimating effect by reflecting light having a greater incident angle back towards the extended illumination source 114 so that the light is recycled. Liquid crystal displays (LCDs) often include brightness enhancing prism films (typically crossed prism films) to increase an on-axis brightness of the display. In some cases, such films can be omitted when a collimating reflective polarizer is included. In some embodiments of the display system 1000, 1000' there are no brightness enhancing prism films disposed between the display panel 110 and a back reflector (e.g., reflector 117 depicted in FIGS. 5A-5B) of the extended illumination source 114.

Figure 5B:
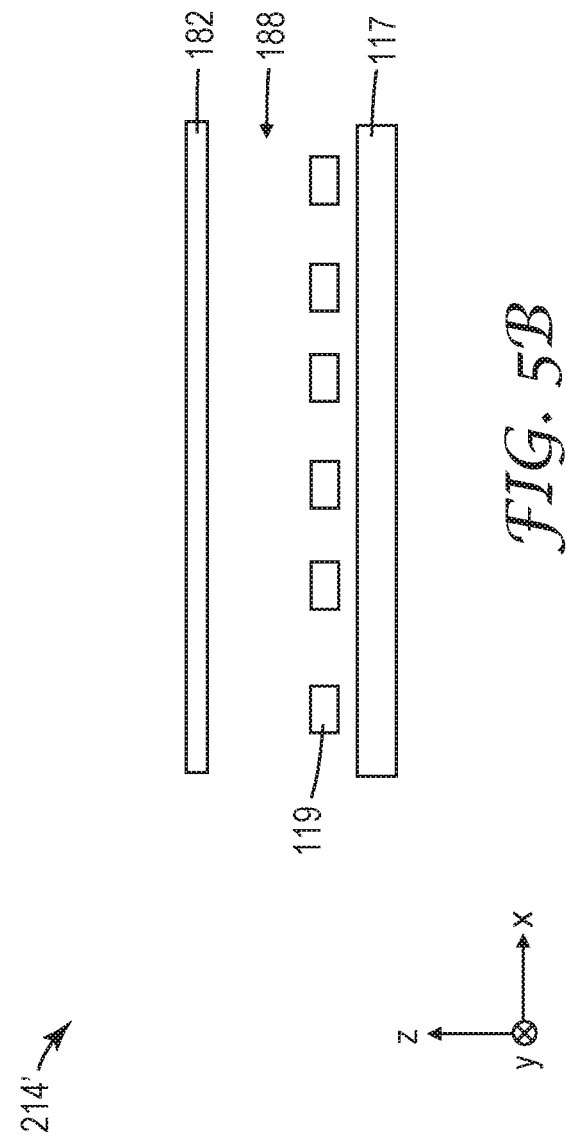

FIGS. 5A-5B are schematic cross-section views of extended illumination sources 214 and 214', respectively, either of which may correspond to extended illumination source 114, according to some embodiments. In some embodiments, the extended illumination source 214 includes a lightguide 113, at least one light source 119, and a reflector 117, where the lightguide 113 is disposed between the reflector 117 and the reflective polarizer 200. The at least one light source 119 may be a plurality of light sources (e.g., light emitting diodes) disposed along edge(s) of the lightguide 113. In some embodiments, the extended illumination source 214' includes a reflector 117; an optical diffuser 182 adjacent the reflector 117, where the optical diffuser 182 and the reflector 117 are substantially coextensive with each other in length and width and define an optical cavity 188 therebetween; and at least one light source 119 disposed in the optical cavity.

Layers or elements can be described as substantially coextensive with each other in length and width if at least about 60% of the length and width of each layer or element is co-extensive with at least about 60% of the length and width of each other layer or element. In some embodiments, for layers or elements described as substantially coextensive with each other in length and width, at least about 80% or at least about 90% of each layer or element is co-extensive in length and width with at least about 80% or at least about 90% of the length and width of each other layer or element.

FIG. 6 is a schematic cross-sectional view of a reflective polarizer 200 including a plurality of alternating polymeric layers 141, 142 which may number at least 10 in total or at least 100 in total, where each polymeric layer 141, 142 has an average thickness less than about 500 nm, according to some embodiments. The reflective polarizer may include other layers (e.g., skin layer(s) or protective boundary layer(s)) having a thickness greater than about 500 nm or greater than about 1 micrometer, or greater than about 2 micrometers. The number of layers 141, 142 may be substantially greater than schematically illustrated in FIG. 6. In some embodiments, a total number of the plurality of alternating polymeric layers 141, 142 is in a range of 500 to 1200. The transmission spectra for the reflective polarizer 200 may be specified for substantially normally incident light 150 and for orthogonal first (e.g., block) and second (e.g., pass) polarization states 151 and 152, respectively. The transmission spectra may alternatively, or in addition, be specified for p-polarized (polarized in plane of incidence) and/or s-polarized (polarized orthogonal to plane of incidence) light at oblique angles of incidence, as described further elsewhere herein.

As is known in the art, multilayer optical films, such as reflective polarizer films, which include alternating polymeric layers can be used to provide desired reflection and transmission in desired wavelength ranges by suitable selection of layer thicknesses and refractive index differences. Multilayer optical films and methods of making multilayer optical films are described in U.S. Pat. No. 5,882,774 (Jonza et al.); U.S. Pat. No. 6,179,948 (Merrill et al.); U.S. Pat. No. 6,783,349 (Neavin et al.); U.S. Pat. No. 6,967,778 (Wheatley et al.); and U.S. Pat. No. 9,162,406 (Neavin et al.), for example. Reflective polarizers having sharp band edges are known in the art and are described in U.S. Pat. No. 6,967,778 (Wheatley et al.), for example. In some embodiments, the reflective polarizer 200 is a collimating reflective polarizer. Collimating reflective polarizers are known in the art and are described in U.S. U.S. Pat. No. 9,441,809 (Nevitt et al.) and U.S. Pat. No. 9,551,818 (Weber et al.), for example. Suitable materials for the reflective polarizers of the present description include the polymers described in these references. For example, the reflective polarizer can include alternating substantially isotropic low index layers (e.g., amorphous polyester) and oriented high index layers (e.g., birefringent naphthalene-based polyester).

Figure 7:
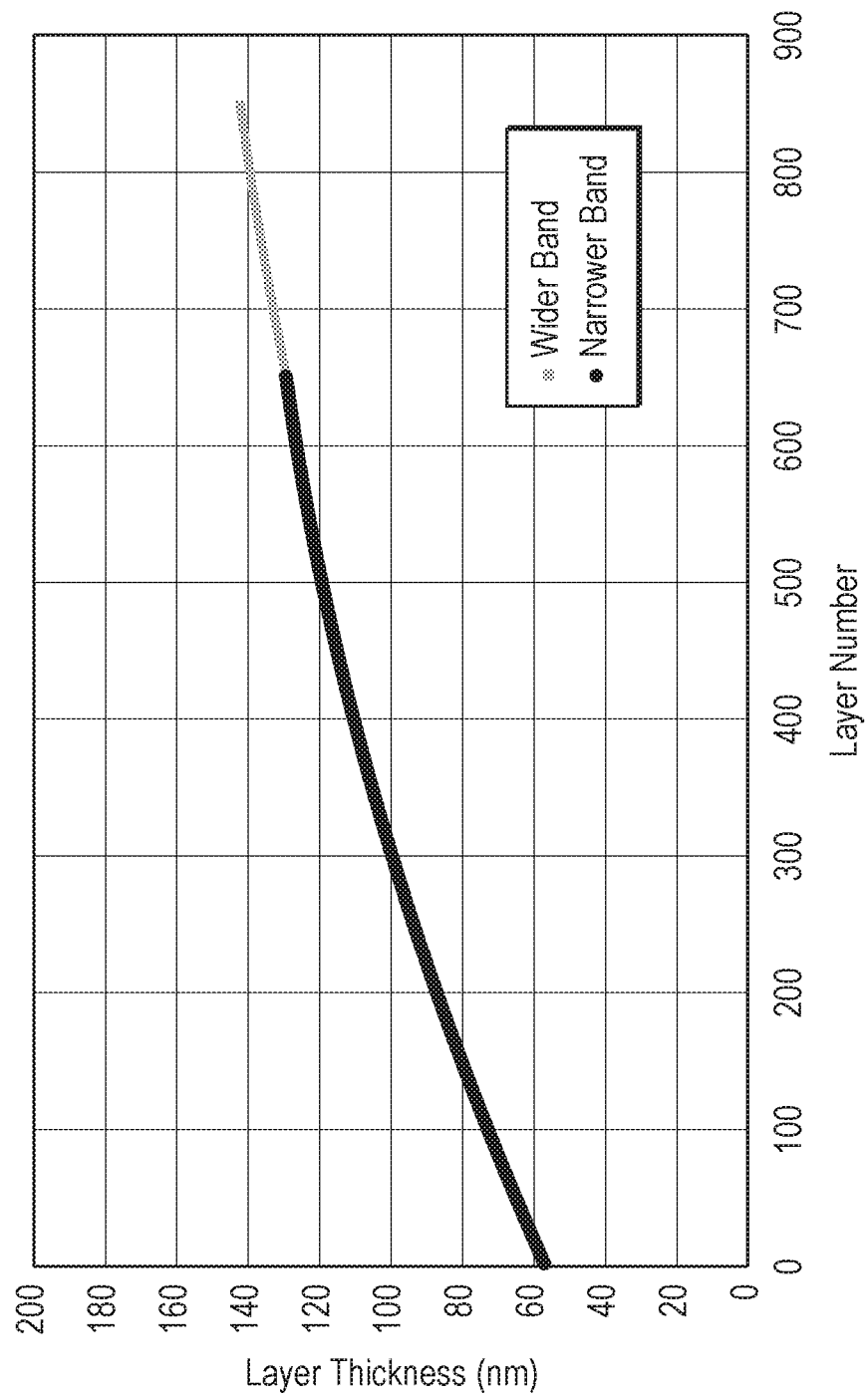
FIG. 7 shows layer thickness profiles for exemplary reflective polarizers.

FIG. 7 is a plot of layer thickness profiles for exemplary reflective polarizers. The layer thickness profile refers to layer thickness versus layer number when the alternating polymeric layers 141, 142 are sequentially numbered from one side of the reflective polarizer to the opposite side. Layer thickness profiles for a narrower band and a wider band reflective polarizer are shown. The narrower band reflective polarizer included a total of 650 alternating polymeric layers 141, 142 and had a band edge wavelength for substantially normally incident light 150 and for a first (e.g., block) polarization state 151 of 901 nm. The wider band reflective polarizer included a total of 850 alternating polymeric layers 141, 142 and had a band edge wavelength for substantially normally incident light 150 and for a first (e.g., block) polarization state 151 of 986 nm.

In some embodiments, the layer thickness profile is selected to provide a transmission spectrum including a concave down portion in a visible wavelength range or a visible-near infrared wavelength range and a sharp band edge separating the visible wavelength range or visible-near infrared wavelength range from a near infrared range. In some embodiments, the layer thickness profile is substantially monotonically increasing from a thinnest polymeric layer adjacent one side of the reflective polarizer to a thickest polymeric layer adjacent the opposite side of the reflective polarizer where the layer thickness profile has a generally concave down shape as shown in FIG. 7.

FIGS. 8A-8B are schematic illustrations of light incident on reflective polarizer 200 in different planes of incidence. Light 150 is substantially normally incident on the reflective polarizer 200 and light 159, 159' is incident on the reflective polarizer 200 at an angle of incidence of θ. In FIG. 8A, light 159 is incident on the reflective polarizer 200 in a plane of incidence parallel to the x-z plane and in FIG. 8B, light 159' is incident on the reflective polarizer 200 in a plane of incidence parallel to the y-z plane. The first polarization state 151 can be described as the polarization state where the electric field projected onto the plane (x-y plane) of the reflective polarizer 200 is along a block axis (x-axis), and the second polarization state 152 can be described as the polarization state where the electric field projected onto the plane (x-y plane) of the reflective polarizer 200 is along a pass axis (y-axis). In the x-z plane of incidence (FIG. 8A), the first polarization state 151 is a p-polarization state and the second polarization state 152 is an s-polarization state. In the y-z plane of incidence (FIG. 8B), the first polarization state 151 is an s-polarization state and the second polarization state 152 is a p-polarization state.

Figure 9:
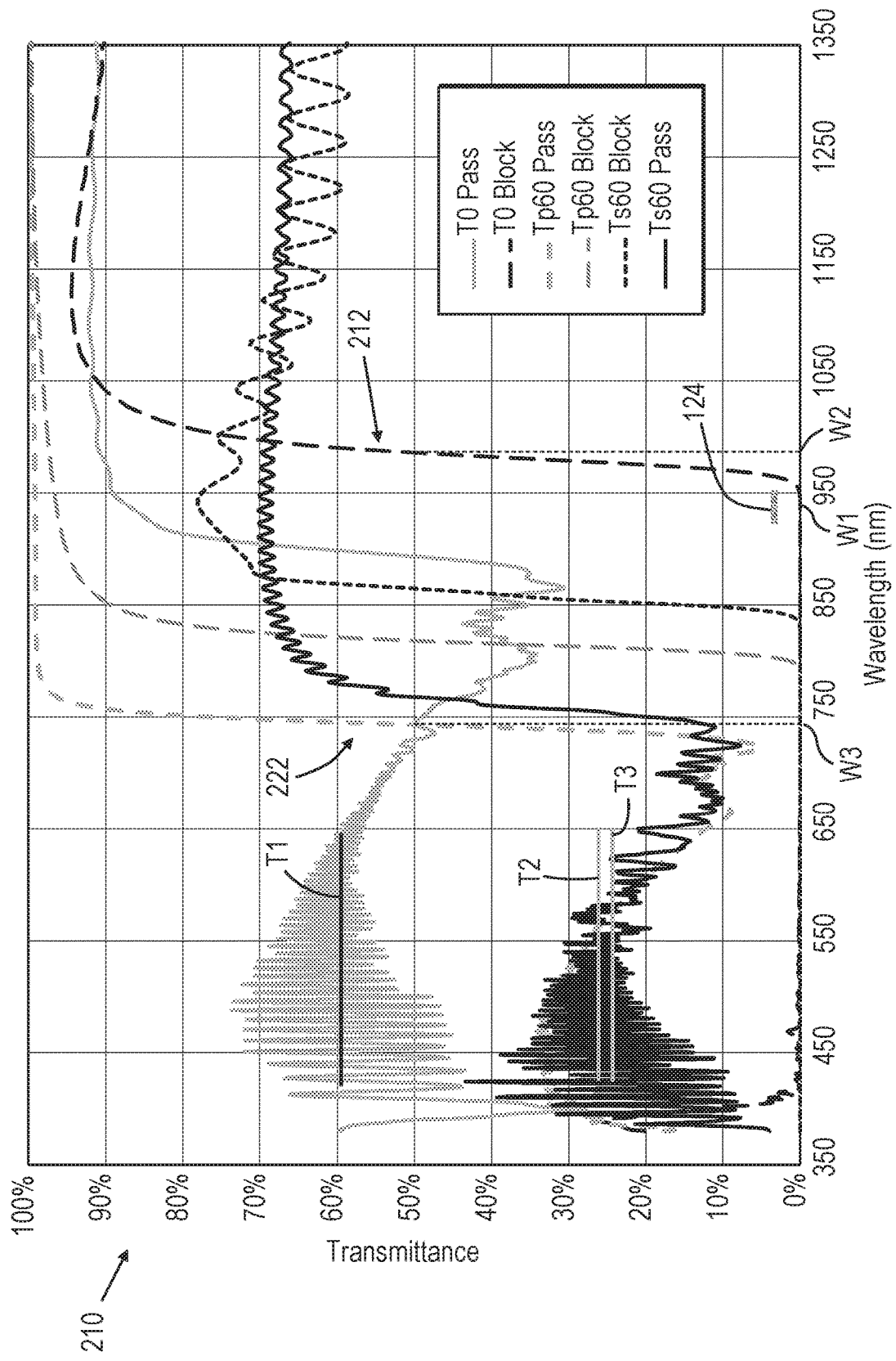
FIG. 9 is a plot of transmittance of an exemplary reflective polarizer for various polarization states and incidence angles.

FIG. 9 is a plot of transmittance of an exemplary reflective polarizer for various polarization states and incidence angles. TO Block and TO Pass denote transmittance for normally incident light having the first (151) and second (152) polarization states, respectively. Tp60 Block and Ts60 Block denote transmittance for light incident on the reflective polarizer at an angle of incidence of 60 degrees in the first polarization state 151 for planes of incidence parallel and orthogonal, respectively, to the first polarization state 151. Tp60 Pass and Ts60 Pass denote transmittance for light incident on the reflective polarizer at an angle of incidence of 60 degrees in the second polarization state 152 for planes of incidence parallel and orthogonal, respectively, to the second polarization state 152. The reflective polarizer of FIG. 9 used the layer thickness profile shown in FIG. 7 for the wider band case. The transmission spectra for a reflective polarizer using the layer thickness profile shown in FIG. 7 for the narrower band case appears similarly but with the band edges shifted to lower wavelengths. The transmission spectra shown in FIG. 9 were calculated using conventional optical modeling techniques. The alternating layers 141, 142 were modeled as including low index layers of an amorphous polyester (glycol-modified polyethylene terephthalate (PETg)) and high index layers of oriented polyethylene naphthalate (PEN). The low index layers were modeled as isotropic with a refractive index at 633 nm of 1.563 and the high index layers were modeled as having refractive indices at 633 nm of 1.804 in the x-direction, 1.615 in the y-direction, and 1.51 in the z-direction. The reflective polarizer was modeled as including 500 nm thick PETg skin layers on each side of the reflective polarizer.

The optical transmittance 210 of FIG. 9 includes band edges 212 and 222. Either one of the band edges 212 and 222 may be referred to as a first band edge and the other one of the band edges 212 and 222 may be referred to as a second band edge. In some embodiments, for substantially normally incident light 150 and for a first polarization state 151, an optical transmittance 210 of the reflective polarizer 200 has a first band edge 212 separating first and second wavelength ranges, where the first wavelength range extends at least from about 450 nm to about 900 nm and the second wavelength range extends at least from about 1100 nm to about 1300 nm. The first band edge 212 has a band edge wavelength W2 corresponding to an optical transmittance of about 50% along the first band edge 212. For substantially normally incident light 150 and for the first polarization state 151, the reflective polarizer 200 has an average optical transmittance in the first wavelength range of less than about 10% and an average optical transmittance in the second wavelength range of greater than about 80%. For substantially normally incident light 150 and for a second polarization state 152 orthogonal to the first polarization state 151, the reflective polarizer has an average optical transmittance in the first wavelength range of greater than about 40% and an average optical transmittance in the second wavelength range of greater than about 80%. In some embodiments, for substantially normally incident light 150 and for the second polarization state 152, the reflective polarizer has an average optical transmittance in a wavelength range of from about 450 nm to about 650 nm of about 50% to about 70%. In some embodiments, for substantially normally incident light 150 and for the first polarization state 151, the average optical transmittance of the reflective polarizer 200 in the first wavelength range is less than about 5% or less than about 3%, or less than about 2%. In some such embodiments, or in other embodiments, for substantially normally incident light 150 and for the first polarization state 151, the average optical transmittance in the second wavelength range is greater than about 85% or greater than about 90%.

In some embodiments, the first wavelength range extends at least from about 450 nm to about 925 nm or to about 940 nm, or to about 950 nm. In some embodiments, the first wavelength range extends at least from about 425 nm to about 900 nm, or to about 925 nm or to about 940 nm, or to about 950 nm. In some such embodiments, or in other embodiments, the second wavelength range extends at least from about 1100 nm to about 1350 nm or at least from about 1050 nm to about 1350 nm.

The wavelength W1 of infrared light 127 emitted by an infrared light source 125 is indicated in FIG. 9 as is a full-width at half-maximum 124 of a pass band of an optical filter 122. In some embodiments, W1<975 nm, or W1<960 nm, or W1<950 nm. In some embodiments, W2>W1. In some embodiments, W2−W1>10 nm, or 20 nm, or 30 nm. In some such embodiments, or in other embodiments, W2>960 nm and W1<950 nm.

Figure 10:
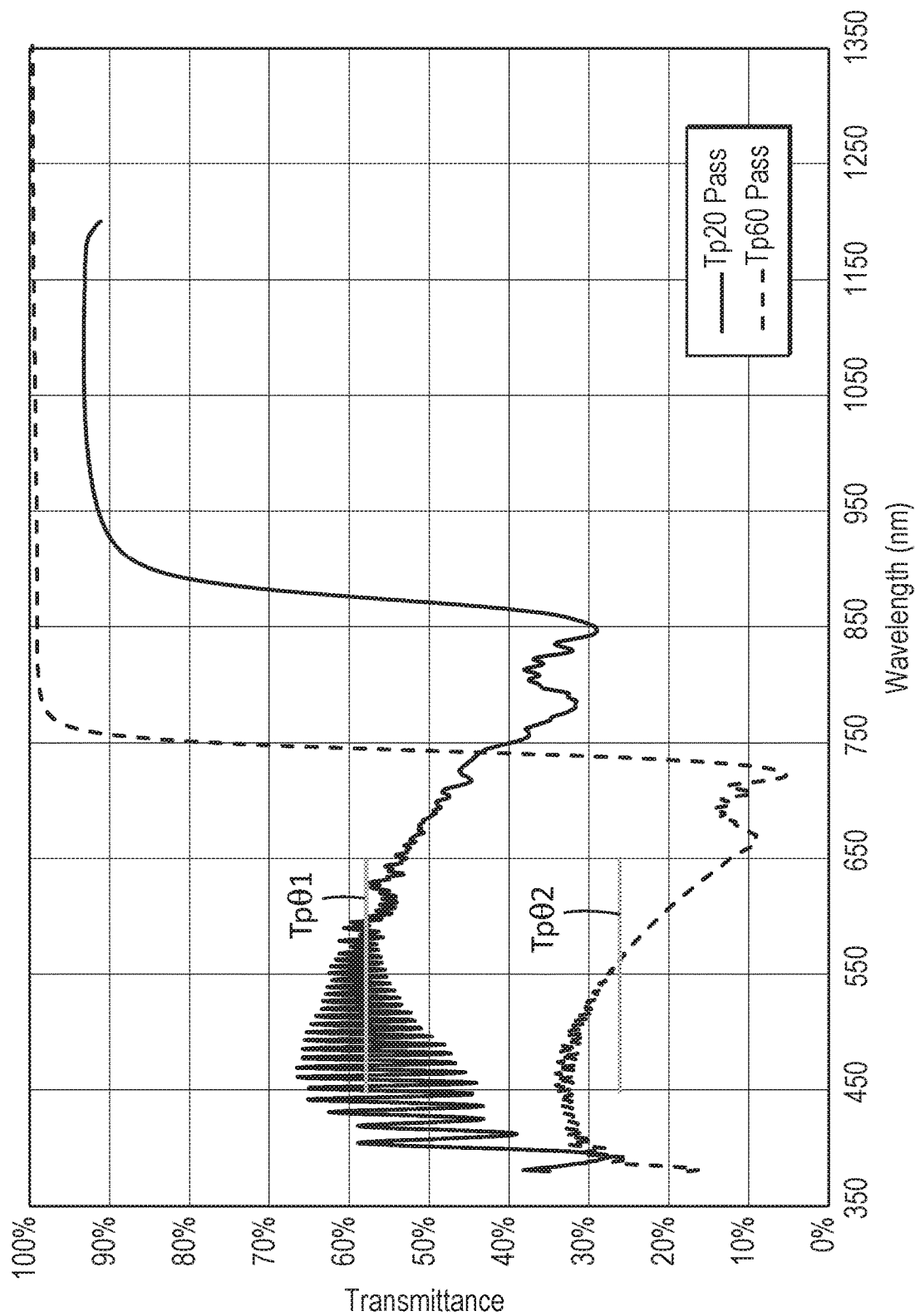
FIG. 10 is a plot of transmittance of an exemplary reflective polarizer for angles of incidence of 20 degrees and 60 degrees.

FIG. 10 is a plot of transmittance of the reflective polarizer of FIG. 9 for a p-polarization state and angles of incidence of 20 degrees and 60 degrees. Tp20 Pass and Tp60 Pass denote transmittance for light incident on the reflective polarizer at an angle of incidence of 20 degrees and 60 degrees, respectively, for the second polarization state 152 and a plane of incidence parallel to the second polarization state 152. In some embodiments, for the second polarization state 152 and a plane of incidence parallel to the second polarization state 152 and for a wavelength range extending at least from about 450 nm to about 650 nm, the reflective polarizer has a greater average optical transmittance Tpθ1 for light incident at a smaller incident angle (e.g., 20 degrees, or 10 degrees, or 5 degrees) and a smaller average optical transmittance Tpθ2 for light incident at a greater incident angle (e.g., 40 degrees, or 50 degrees, or 60 degrees, or 70 degrees). In some embodiments, a difference between the greater average optical transmittance Tpθ1 and the smaller average optical transmittance Tpθ2 is greater than about 20% or greater than about 25%, the smaller incident angle is less than about 25 degrees, and the greater incident angle is in a range of about 40 degrees to about 70 degrees (e.g., about 60 degrees). In some embodiments, for substantially normally incident light 150 and for the second polarization state 152, the reflective polarizer 200 has an average optical transmittance in a third wavelength range of from about 450 nm to about 650 nm of about 50% to about 70%. In some such embodiments, or in other embodiments, for the second polarization state 152 and for light incident on the reflective polarizer at an angle of incidence of about 60 degrees in a plane of incidence parallel to the second polarization state 152, the reflective polarizer has an average optical transmittance in the third wavelength range of about 15% to about 35% or in a range of about 20% to about 30%.

In some embodiments, for substantially normally incident light 150 and for the second polarization state 152, the reflective polarizer 200 has an average optical transmittance T1 in a third wavelength range extending from about 425 nm to about 650 nm; and for the second polarization state 152 and for light 159' incident on the reflective polarizer at an angle of incidence of about 60 degrees in a plane of incidence parallel to the second polarization state 152, the optical transmittance 210 of the reflective polarizer has a second band edge 222 separating the third wavelength range from a fourth wavelength range extending at least from about 850 nm to about 1100 nm.

Figure 11:
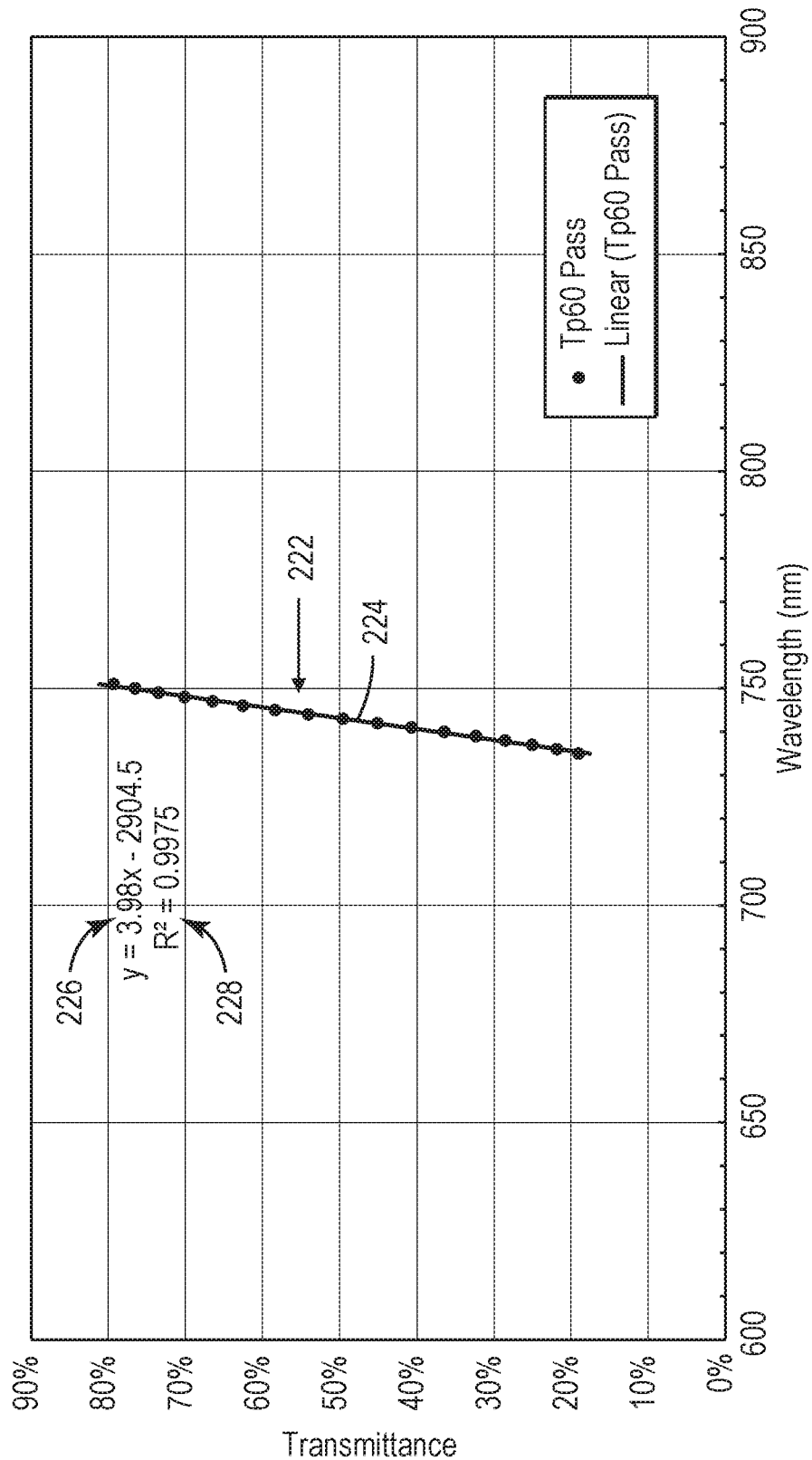
FIG. 11 is a plot of a band edge of an exemplary reflective polarizer for an angle of incidence of 60 degrees.
Figure 12:
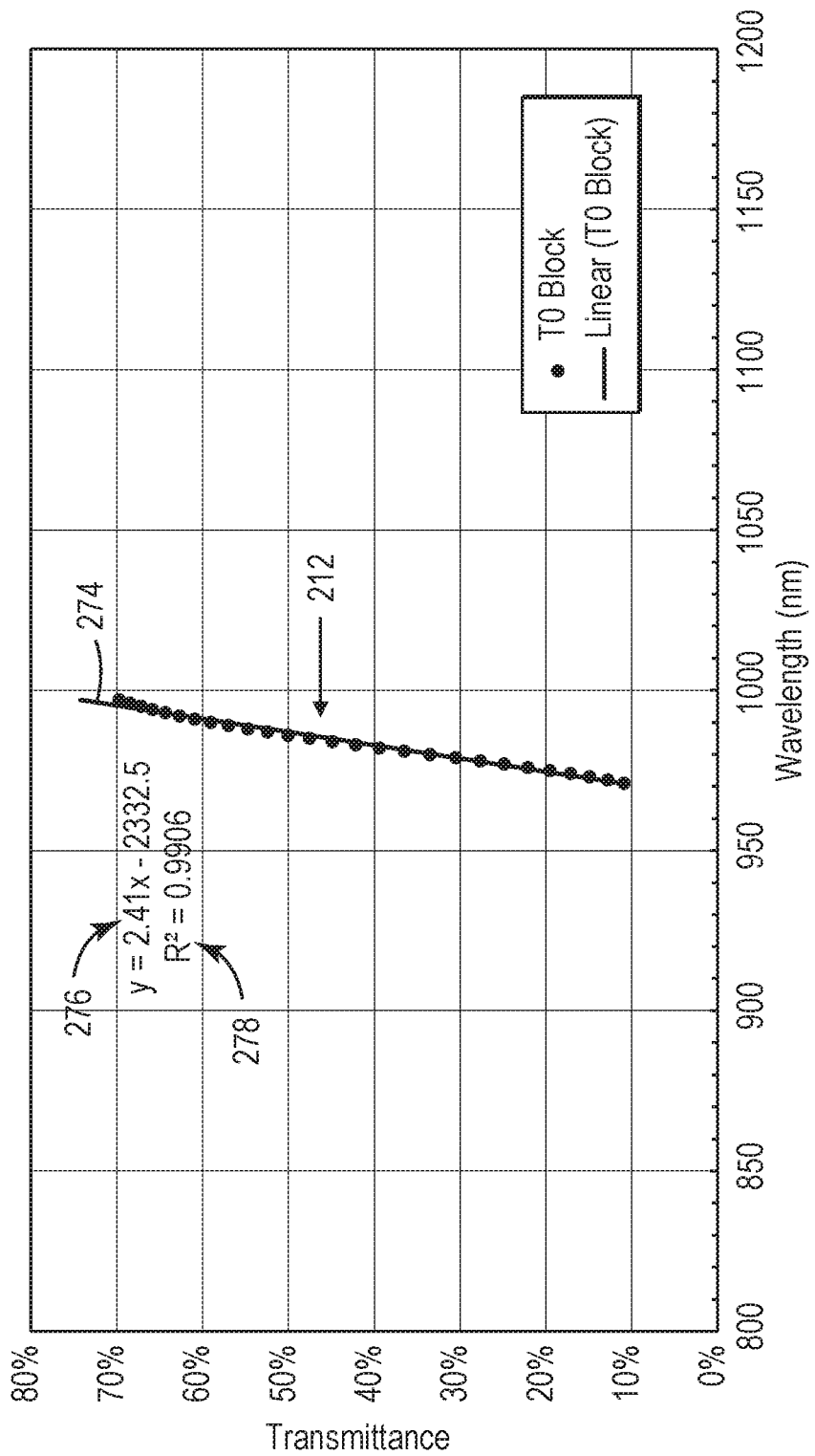
FIG. 12 is a plot of a band edge of an exemplary reflective polarizer for normally incident light.
Figure 13:
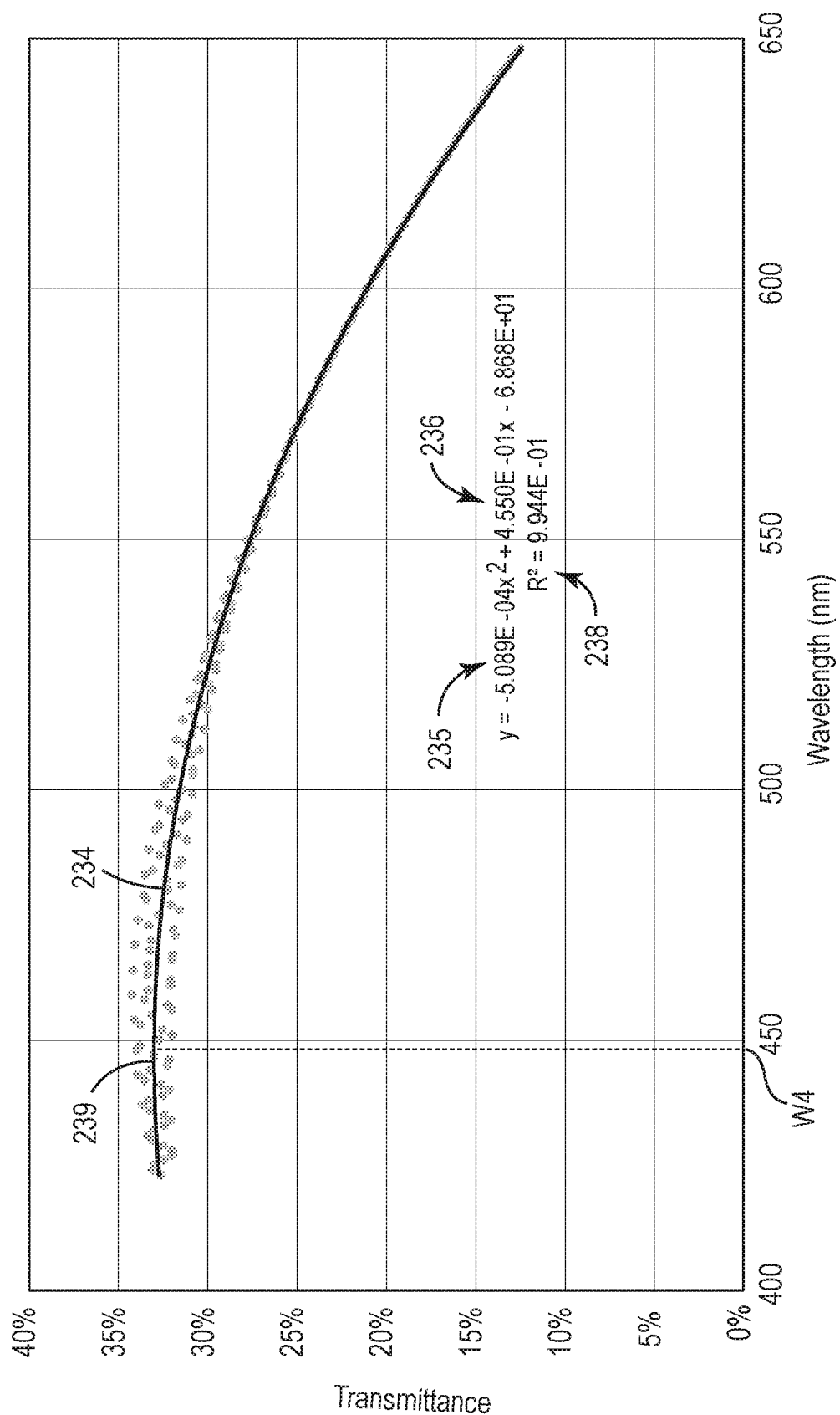
FIG. 13 is a plot of transmittance of an exemplary reflective polarizer for an angle of incidence of 60 degrees.

In some embodiments, the optical transmittance 210 includes a generally concave down portion in the third wavelength range and sharp band edge(s). Such transmission spectra have been found to result in low color shift with view angle. FIGS. 11-12 are plots of portions of the optical transmittance 210 showing the band edges 222 and 212, respectively, and best linear fits 224 and 274, respectively, to the band edges. FIG. 13 is a plot of another portion of the optical transmittance 210 for the second polarization state 152 and light incident on the reflective polarizer in a plane of incidence parallel to the second polarization state 152 at an angle of incidence of 60 degrees. In some embodiments, a best linear fit 224 to the second band edge 222 correlating the optical transmittance 210 to wavelength at least across a wavelength range where the optical transmittance increases from about 20% to about 80% has a slope 226 of greater than about 3%/nm and an r-squared value 228 of greater than about 0.9. In some embodiments, a best second order polynomial fit 234 to the optical transmittance 210 in the third wavelength range has a negative second order coefficient 235 and an r-squared value 238 of greater than about 0.9. In some embodiments, for the second polarization state 152 and for light 159' incident on the reflective polarizer at an angle of incidence of about 60 degrees in a plane of incidence parallel to the second polarization state 152, the reflective polarizer 200 has an average optical transmittance T2 in the third wavelength range from about 15% to about 35% and an average optical transmittance in the fourth wavelength range greater than about 80%, where T1−T2≥10% or T1−T2 can be in a range described elsewhere herein. In some embodiments, the slope 226 is greater than about 3.5%/nm or greater than about 3.7%/nm. In some such embodiments, or in other embodiments, the r-squared value 228 is greater than about 0.95, or greater than about 0.98.

In some embodiments, the reflective polarizer 200 includes a plurality of alternating polymeric layers 141, 142 numbering at least 10 in total, where each polymeric layer has an average thickness less than about 500 nm, such that:
  for substantially normally incident light:
    for a first polarization state 151, the reflective polarizer 200 has an average optical transmittance in a first wavelength range extending from about 425 nm to about 650 nm of less than about 5%; and
    for a second polarization state 152 orthogonal to the first polarization state 151, the reflective polarizer 200 has an average optical transmittance T1 in the first wavelength range of greater than about 40%; and
  for light incident on the reflective polarizer at an angle of incidence of about 60 degrees:
    for the first polarization state 151 and a plane of incidence parallel to the first polarization state 151 (see, e.g., FIG. 8A), the reflective polarizer 200 has an average optical transmittance in the first wavelength range of less than about 5%; and
    for the second polarization state 152 and a plane of incidence parallel to the second polarization state 152 (see, e.g., FIG. 8B), an optical transmittance 210 of the reflective polarizer 200 has a first band edge 222 separating the first wavelength range and a second wavelength range extending at least from about 850 nm to about 1100 nm, where a best linear fit 224 to the first band edge correlating the optical transmittance to wavelength at least across a wavelength range where the optical transmittance increases from about 20% to about 80% has a slope 226 of greater than about 3%/nm and an r-squared value 228 of greater than about 0.9, a best second order polynomial fit 234 to the optical transmittance in the first wavelength range has a negative second order coefficient 235 and an r-squared value 238 of greater than about 0.9, and the reflective polarizer 200 has an average optical transmittance T2 in the first wavelength range from about 15% to about 35% and an average optical transmittance in the second wavelength range greater than about 80%. In some embodiments, T1−T2≥10%.

In some embodiments, for the first polarization state 151 and for light incident on the reflective polarizer 200 at an angle of incidence of about 60 degrees in a plane of incidence (e.g., y-z plane) orthogonal to the first polarization state 151, the reflective polarizer 200 has an average optical transmittance in the first wavelength range of less than about 5%. In some embodiments, for the second polarization state 152 and for light incident on the reflective polarizer 200 at an angle of incidence of about 60 degrees in a plane of incidence (e.g., x-y plane) orthogonal to the second polarization state 152, the reflective polarizer 200 has an average optical transmittance T3 in the first wavelength range from about 15% to about 35% and an average optical transmittance in the second wavelength range greater than about 60%. In some embodiments, T2 and T3 are each in a range of about 20% to about 30%. In some embodiments, |T3−T2|≤8% or |T3−T2|≤5%.

In some embodiments, T1 is in a range of about 50% to about 70%. In some such embodiments, or in other embodiments, T1−T2≥15%, or T1−T2≥20%, or T1−T2≥25%. In some such embodiments, or in other embodiments, T1−T2≤60%, or T1−T2≤50%, or T1−T2≤40%.

In some embodiments, the first band edge 222 has a first band edge wavelength W3 corresponding to an optical transmittance of about 50% along the first band edge 222, where the first band edge wavelength W3 is at least about 670 nm, or at least about 700 nm, or at least about 720 nm.

In some embodiments, for substantially normally incident light and for the first polarization state 151, the reflective polarizer 200 has an average optical transmittance in the first wavelength range of less than about 3% or less than about 2%. In some embodiments, for light incident on the reflective polarizer 200 at an angle of incidence of about 60 degrees and for the first polarization state 151 and a plane of incidence parallel to the first polarization state 151, the reflective polarizer 200 has an average optical transmittance in the first wavelength range of less than about 3%, or less than about 2%. In some embodiments, for substantially normally incident light 150 and for the first polarization state, an optical transmittance 210 of the reflective polarizer 200 has a second band edge 212 separating third and fourth wavelength ranges, where the third wavelength range extends at least from about 450 nm to about 900 nm, and the fourth wavelength range extends at least from about 1100 nm to about 1300 nm, and where the reflective polarizer 200 has an average optical transmittance in the third wavelength range of less than about 5% and an average optical transmittance in the fourth wavelength range of greater than about 80%. In some embodiments, for substantially normally incident light 150 and for the first polarization state, the reflective polarizer 200 has an average optical transmittance in the third wavelength range of less than about 3%, or less than about 2%. In some embodiments, for substantially normally incident light 150 and for the first polarization state, the reflective polarizer 200 has an average optical transmittance in the fourth wavelength range of greater than about 85% or greater than about 90%.

In some embodiments, the third wavelength range extends at least from about 450 nm to about 925 nm or to about 940 nm, or to about 950 nm. In some embodiments, the third wavelength range extends at least from about 425 nm to about 900 nm, or to about 925 nm or to about 940 nm, or to about 950 nm. In some such embodiments, or in other embodiments, the fourth wavelength range extends at least from about 1100 nm to about 1350 nm or at least from about 1050 nm to about 1350 nm.

In some embodiments, for substantially normally incident light 150 and for the second polarization state 152, the reflective polarizer has an average optical transmittance in the fourth wavelength range of greater than about 80%. In some embodiments, the second band edge 212 has a second band edge wavelength W2 corresponding to an optical transmittance of about 50% along the second band edge, where the second band edge wavelength W2 is in a range of about 925 nm to about 1050 nm. In some embodiments, a best linear fit 274 to the second band edge 212 correlating the optical transmittance to wavelength at least across a wavelength range where the optical transmittance increases from about 10% to about 70% has a slope 276 of greater than about 2%/nm and an r-squared value 278 greater than about 0.9. In some embodiments, the slope 226 of the best linear fit 224 to the first band edge 222 is greater than the slope 276 of the best linear fit 274 to the second band edge 212 by at least about 0.5%/nm, or by at least 0.7%/nm, or by at least 1%/nm. In some embodiments, the slope 276 is greater than about 2.2%/nm or greater than about 2.3%/nm. In some such embodiments, or in other embodiments, the r-squared value 278 is greater than about 0.95, or greater than about 0.98.

In some embodiments, the best second order polynomial fit 234 has a positive first order coefficient 236. In some embodiments, the best second order polynomial fit 234 has a maximum 239 at a wavelength W4 between about 400 nm and about 550 nm, or between about 425 nm and about 500 nm. In some embodiments, the r-squared value 238 is greater than about 0.95, or greater than about 0.98.

Figure 14:
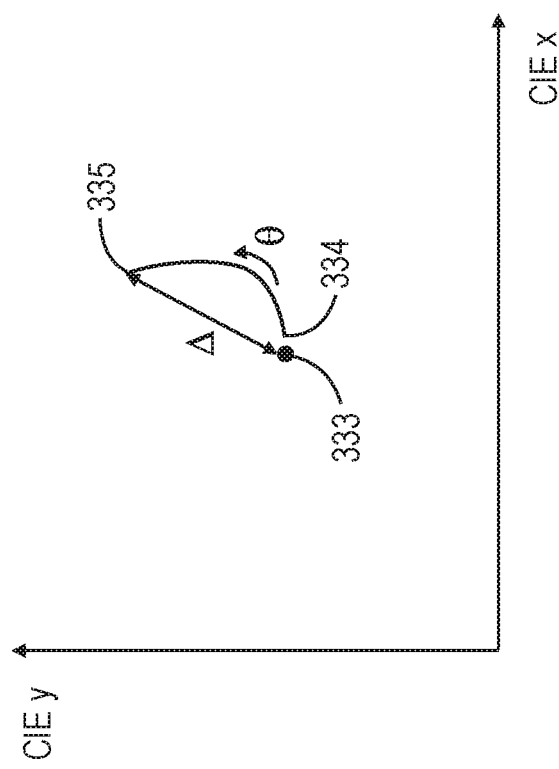
FIG. 14 schematically illustrates color shift with angle of incidence in CIE xy color space.

FIG. 14 is a schematic plot on a CIE (Commission Internationale de l'éclairage) 1931 xy color space illustrating color shift with incidence angle θ for light in the second polarization state 152 incident on a reflective polarizer 200. The incident light can be a substantially white light represented by point 333. The substantially white light can have CIE 1931 xy coordinates each in a range of 0.29 to 0.35, or 0.3 to 0.34, for example. The substantially white light can be standard illuminant D65, for example, which has CIE 1931 x and y coordinates of 0.3127 and 0.329, respectively. The color can shift from a point 334 closer to the point 333 at a low or zero angle of incidence to a point 335 farther from the point 333 at a high angle of incidence. In some embodiments, the reflective polarizer 200 is configured such that for substantially white incident light (e.g., represented by point 333) and for the second polarizations state 152, a maximum difference Δ in color between light transmitted through the reflective polarizer and the incident light as an angle of incidence θ of the incident light varies from zero to about 60 degrees in each of a plane of incidence parallel to the second polarization state 152 and a plane of incidence orthogonal to the second polarization state 152 is no more than about 0.07, or no more than about 0.06, or no more than about 0.05 on a CIE 1931 xy color space. In some embodiments, the reflective polarizer 200 is configured such that for substantially white incident light and for the second polarizations state 152, a maximum difference Δ in color between light transmitted through the reflective polarizer 200 and the incident light as an angle of incidence θ of the incident light varies from zero to about 75 degrees in each of a plane of incidence parallel to the second polarization state 152 and a plane of incidence orthogonal to the second polarization state 152 is no more than about 0.08, or no more than about 0.07, or no more than about 0.06, or no more than about 0.05 on a CIE 1931 xy color space.

For the reflective polarizer having the transmission spectra of FIG. 9, for standard illuminant D65 light and for the second polarizations state 152, a calculated difference Δ in color between incident light and light transmitted through the reflective polarizer for an angle of incidence of 60 degrees was 0.0495 for the plane of incidence parallel to the second polarization state 152 (p-polarized light) and 0.0203 for the plane of incidence orthogonal to the second polarization state 152 (s-polarized light).

To test the robustness of the low color shift against manufacturing variations that could result in reduced thickness and band edges shifted to lower wavelengths, the color shifts for reflective polarizers having the layer thickness profiles of FIG. 7 corresponding to the narrower and wider bands were calculated and the color shifts for reflective polarizers having thickness reduced by 5% or by 10% were calculated. The incident light had the spectrum of red, green, and blue light emitting diodes having relative intensities selected to give CIE 1931 x and y coordinates of 0.3127 and 0.329, respectively. The color shift in CIE 1931 xy color space was calculated for the reduced thickness (95% thickness and 90% thickness) reflective polarizer relative to the corresponding reflective polarizer at 100% thickness for an angle of incidence of 60 degrees and for the second polarization state 152. For the wider band reflective polarizer, the color shift was less than 0.044 for 95% thickness and 90% thickness and for each of planes of incidence parallel and orthogonal to the second polarization state 152. For the narrower band reflective polarizer, the color shift was 0.0924 for 90% thickness and for a plane of incidence (s-polarization) orthogonal to the second polarization state 152, and was 0.1682 for 90% thickness and for a plane of incidence (p-polarization) parallel to the second polarization state 152. These large color shifts were primarily due to an increase in the CIE x coordinate indicating a shift toward the red. The results indicate that the wider band reflective polarizer provides a low color shift that is more robust against manufacturing variations than that of the narrower band reflective polarizer.

The best linear fits described herein can be linear least squares fits as is known in the art. Best polynomial fits can similarly be least squares fits. Such fits minimize the sum of squares of residuals where a residual is the difference between data and the fitted curve (line or polynomial). The least squares analysis allows the r-squared value, sometimes referred to as the coefficient of determination, to be determined.

Terms such as "about" will be understood in the context in which they are used and described in the present description by one of ordinary skill in the art. If the use of "about" as applied to quantities expressing feature sizes, amounts, and physical properties is not otherwise clear to one of ordinary skill in the art in the context in which it is used and described in the present description, "about" will be understood to mean within 10 percent of the specified value. A quantity given as about a specified value can be precisely the specified value. For example, if it is not otherwise clear to one of ordinary skill in the art in the context in which it is used and described in the present description, a quantity having a value of about 1, means that the quantity has a value between 0.9 and 1.1, and that the value could be 1.

Terms such as "substantially" will be understood in the context in which they are used and described in the present description by one of ordinary skill in the art. If the use of "substantially normal" is not otherwise clear to one of ordinary skill in the art in the context in which it is used and described in the present description, "substantially normal" will mean within 20 degrees of normal. Directions described as substantially normal may, in some embodiments, be within 10 degrees, or within 5 degrees of normal, or may be normal or nominally normal.

All references, patents, and patent applications referenced in the foregoing are hereby incorporated herein by reference in their entirety in a consistent manner. In the event of inconsistencies or contradictions between portions of the incorporated references and this application, the information in the preceding description shall control.

Descriptions for elements in figures should be understood to apply equally to corresponding elements in other figures, unless indicated otherwise. Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations, or variations, or combinations of the specific embodiments discussed herein. Therefore, it is intended that this disclosure be limited only by the claims and the equivalents thereof

What is claimed is:

1. A display system for sensing a finger of a user applied to the display system, the display system comprising:
    a display panel configured to generate an image for viewing by the user;
    a sensor for sensing the finger of the user disposed proximate the display panel;
    an infrared light source configured to emit an infrared light having a wavelength W1 toward the finger of the user, the sensor configured to receive and detect at least a portion of the infrared light reflected by the finger; and
    a reflective polarizer disposed between the display panel and the sensor such that for substantially normally incident light:
        for a first polarization state, an optical transmittance of the reflective polarizer comprises a first band edge separating first and second wavelength ranges, the first wavelength range extending at least from about 450 nm to about 900 nm, the second wavelength range extending at least from about 1100 nm to about 1300 nm, the first band edge having a band edge wavelength W2 corresponding to an optical transmittance of about 50% along the first band edge, the reflective polarizer having an average optical transmittance in the first wavelength range of less than about 10% and an average optical transmittance in the second wavelength range of greater than about 80%; and
        for a second polarization state orthogonal to the first polarization state, the reflective polarizer has an average optical transmittance in the first wavelength range of greater than about 40% and an average optical transmittance in the second wavelength range of greater than about 80%,
    wherein W2>W1.

2. The display system of claim 1, wherein the sensor is disposed to receive light reflected from the finger and then incident on the reflective polarizer at an angle of incidence greater than about 40 degrees.

3. The display system of claim 1, wherein W2>960 nm and W1<950 nm.

4. The display system of claim 1, wherein for the second polarization state and a plane of incidence parallel to the second polarization state and for a wavelength range extending at least from about 450 nm to about 650 nm, the reflective polarizer has a greater average optical transmittance for light incident at a smaller incident angle and a smaller average optical transmittance for light incident at a greater incident angle.

5. The display system of claim 4, wherein a difference between the greater average optical transmittance and the smaller average optical transmittance is greater than about 20%, the smaller incident angle is less than about 25 degrees, and the greater incident angle is in a range of about 40 degrees to about 70 degrees.

6. The display system of claim 1, wherein for substantially normally incident light and for the second polarization state, the reflective polarizer has an average optical transmittance T1 in a third wavelength range extending from about 425 nm to about 650 nm; and wherein for the second polarization state and for light incident on the reflective polarizer at an angle of incidence of about 60 degrees in a plane of incidence parallel to the second polarization state, the optical transmittance of the reflective polarizer comprises a second band edge separating the third wavelength range from a fourth wavelength range extending at least from about 850 nm to about 1100 nm, a best linear fit to the second band edge correlating the optical transmittance to wavelength at least across a wavelength range where the optical transmittance increases from about 20% to about 80% having a slope of greater than about 3%/nm and an r-squared value of greater than about 0.9, a best second order polynomial fit to the optical transmittance in the third wavelength range having a negative second order coefficient and an r-squared value of greater than about 0.9, the reflective polarizer having an average optical transmittance T2 in the third wavelength range from about 15% to about 35% and an average optical transmittance in the fourth wavelength range greater than about 80%, T1−T2≥10%.

7. A display system for sensing a finger of a user applied to the display system, the display system comprising:
a display panel configured to generate an image for viewing by the user;
a sensor for sensing the finger of the user disposed proximate the display panel;
an infrared light source configured to emit an infrared light having a wavelength W1<975 nm toward the finger of the user, the sensor configured to receive and detect at least a portion of the infrared light reflected by the finger; and
a reflective polarizer disposed between the display panel and the sensor such that for substantially normally incident light:
for a first polarization state, an optical transmittance of the reflective polarizer comprises a first band edge separating first and second wavelength ranges, the first wavelength range extending at least from about 450 nm to about 900 nm, the second wavelength range extending at least from about 1100 nm to about 1300 nm, the reflective polarizer having an average optical transmittance in the first wavelength range of less than about 10% and an average optical transmittance in the second wavelength range of greater than about 80%; and
for a second polarization state orthogonal to the first polarization state, the reflective polarizer has an average optical transmittance in the first wavelength range of greater than about 40% and an average optical transmittance in the second wavelength range of greater than about 80%,
wherein the reflective polarizer is configured such that for substantially white incident light and for the second polarization state, a maximum difference in color between light transmitted through the reflective polarizer and the incident light as an angle of incidence of the incident light varies from zero to about 60 degrees in each of a plane of incidence parallel to the second polarization state and a plane of incidence orthogonal to the second polarization state is no more than about 0.07 on a CIE 1931 xy color space.

8. The display system of claim 7, wherein the first band edge has a band edge wavelength W2 corresponding to an optical transmittance of about 50% along the first band edge, W2>W1.

9. A reflective polarizer comprising a plurality of alternating polymeric layers numbering at least 10 in total, each polymeric layer having an average thickness less than about 500 nm, such that:
for substantially normally incident light:
for a first polarization state, the reflective polarizer has an average optical transmittance in a first wavelength range extending from about 425 nm to about 650 nm of less than about 5%; and
for a second polarization state orthogonal to the first polarization state, the reflective polarizer has an average optical transmittance T1 in the first wavelength range of greater than about 40%; and
for light incident on the reflective polarizer at an angle of incidence of about 60 degrees:
for the first polarization state and a plane of incidence parallel to the first polarization state, the reflective polarizer has an average optical transmittance in the first wavelength range of less than about 5%; and
for the second polarization state and a plane of incidence parallel to the second polarization state, an optical transmittance of the reflective polarizer comprises a first band edge separating the first wavelength range and a second wavelength range extending at least from about 850 nm to about 1100 nm, a best linear fit to the first band edge correlating the optical transmittance to wavelength at least across a wavelength range where the optical transmittance increases from about 20% to about 80% having a slope of greater than about 3%/nm and an r-squared value of greater than about 0.9, a best second order polynomial fit to the optical transmittance in the first wavelength range having a negative second order coefficient and an r-squared value of greater than about 0.9, the reflective polarizer having an average optical transmittance T2 in the first wavelength range from about 15% to about 35% and an average optical transmittance in the second wavelength range greater than about 80%, T1−T2≥10%.

10. The reflective polarizer of claim 9, wherein the first band edge has a first band edge wavelength corresponding to an optical transmittance of about 50% along the first band edge, the first band edge wavelength being at least about 700 nm.

11. The reflective polarizer of claim 9, wherein for the second polarization state and for light incident on the reflective polarizer at an angle of incidence of about 60 degrees in a plane of incidence orthogonal to the second polarization state, the reflective polarizer has an average optical transmittance T3 in the first wavelength range from about 15% to about 35% and an average optical transmittance in the second wavelength range greater than about 60%.

12. The reflective polarizer of claim 11, wherein |T3−T2|≤5%.

13. The reflective polarizer of claim 9, wherein for substantially normally incident light and for the first polarization state, the optical transmittance of the reflective polarizer comprises a second band edge separating third and fourth wavelength ranges, the third wavelength range extending at least from about 450 nm to about 900 nm, the fourth wavelength range extending at least from about 1100 nm to about 1300 nm, the reflective polarizer having an average optical transmittance in the third wavelength range of less than about 5% and an average optical transmittance in the fourth wavelength range of greater than about 80%.

14. The reflective polarizer of claim 13, wherein the second band edge has a second band edge wavelength corresponding to an optical transmittance of about 50% along the second band edge, the second band edge wavelength being in a range of about 925 nm to about 1050 nm.

15. The reflective polarizer of claim 13, wherein a best linear fit to the second band edge correlating the optical transmittance to wavelength at least across a wavelength range where the optical transmittance increases from about 10% to about 70% has a slope of greater than about 2%/nm and an r-squared value greater than about 0.9.

* * * * *